US007862175B2

(12) United States Patent
Nozawa et al.

(10) Patent No.: US 7,862,175 B2
(45) Date of Patent: Jan. 4, 2011

(54) OPTOMETER

(75) Inventors: Noritsugu Nozawa, Toyokawa (JP);
Hirohisa Terabe, Toyokawa (JP)

(73) Assignee: Nidek Co., Ltd., Gamagori-Shi (JP)

( * ) Notice: Subject to any disclaimer, the term of this patent is extended or adjusted under 35 U.S.C. 154(b) by 0 days.

(21) Appl. No.: 11/511,425

(22) Filed: Aug. 29, 2006

(65) Prior Publication Data
US 2007/0052924 A1 Mar. 8, 2007

(30) Foreign Application Priority Data
Sep. 2, 2005 (JP) .............................. 2005-255768

(51) Int. Cl.
*A61B 3/00* (2006.01)
*A61B 3/10* (2006.01)
*A61B 3/02* (2006.01)

(52) U.S. Cl. .................. 351/245; 351/216; 351/233
(58) Field of Classification Search ................. 351/205, 351/216, 217, 233, 234, 235, 245
See application file for complete search history.

(56) References Cited

U.S. PATENT DOCUMENTS

| 6,923,541 B2 | 8/2005 | Hosoi et al. | |
| 6,961,105 B2* | 11/2005 | Chang et al. | 349/114 |
| 7,152,836 B2* | 12/2006 | Pfister et al. | 248/292.14 |
| 7,363,065 B2* | 4/2008 | Lee | 455/575.3 |
| 2001/0015757 A1* | 8/2001 | Saito | 348/207 |
| 2002/0102946 A1 | 8/2002 | SanGiovanni | |
| 2004/0184001 A1 | 9/2004 | Terabe | |
| 2005/0044510 A1 | 2/2005 | Yi | |
| 2005/0105050 A1 | 5/2005 | Hosoi | |
| 2005/0107138 A1 | 5/2005 | SanGiovanni | |
| 2005/0276164 A1* | 12/2005 | Amron | 368/82 |

FOREIGN PATENT DOCUMENTS

| EP | 1 442 697 A1 | 8/2004 |
| GB | 2 405 068 A | 2/2005 |
| JP | A 09-299332 | 11/1997 |
| JP | A 2002-135380 | 5/2002 |

* cited by examiner

*Primary Examiner*—Jack Dinh
(74) *Attorney, Agent, or Firm*—Oliff & Berridge, PLC

(57) ABSTRACT

An optometer for subjectively examining refractive power of an examinee's eye, comprises: a phoropter which selectively disposes an optical element in front of the examinee's eye; a controller having a switch panel for transmitting a signal to the phoropter and a horizontally extending rotation axis; a display rotatable about the rotation axis of the controller, orientation of the display being changeable by its rotation between a side with the switch panel and a side without the switch panel; and a control part which controls a display screen of the display to appear in a constant orientation irrespective of whether the display is reversed upside down by its rotation.

10 Claims, 10 Drawing Sheets

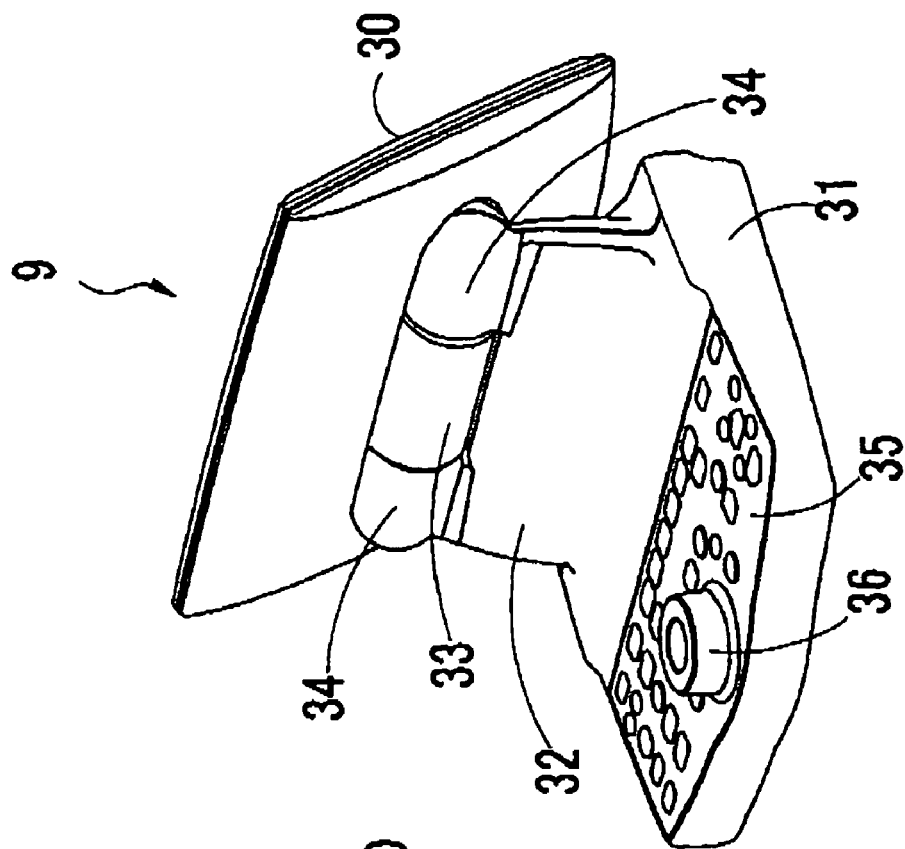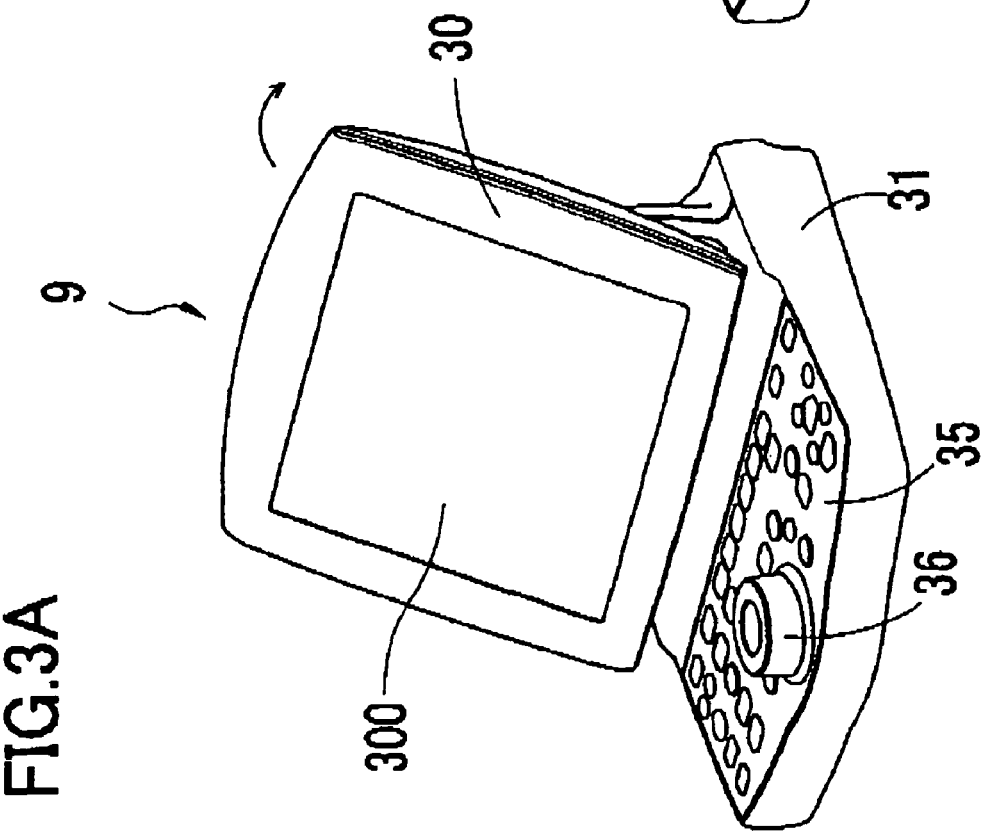
FIG.3A
FIG.3B

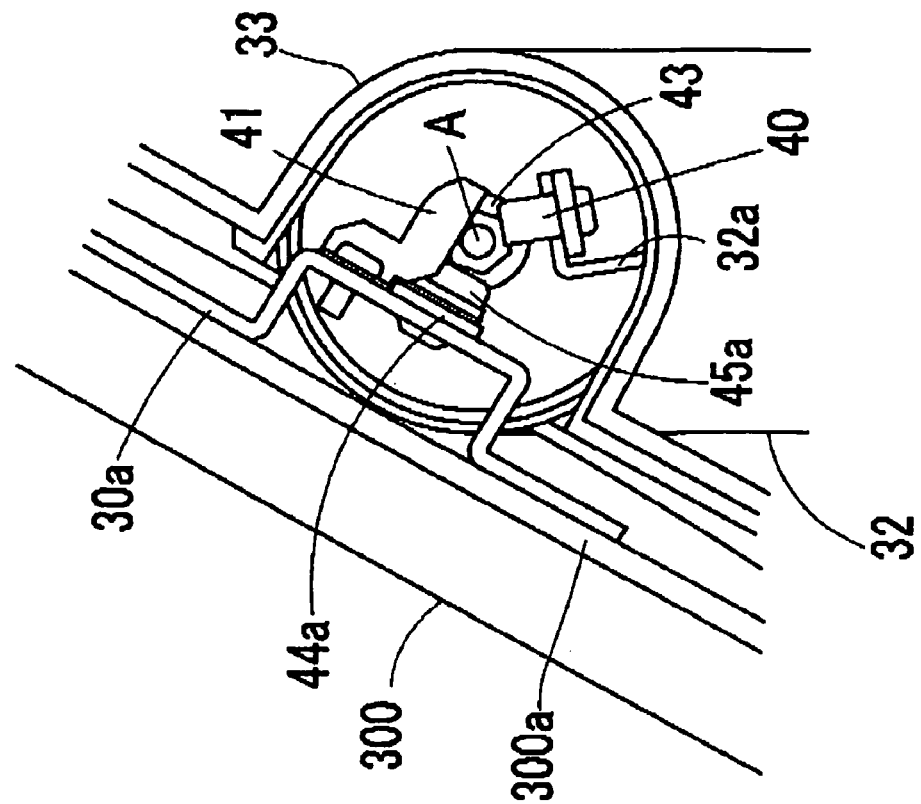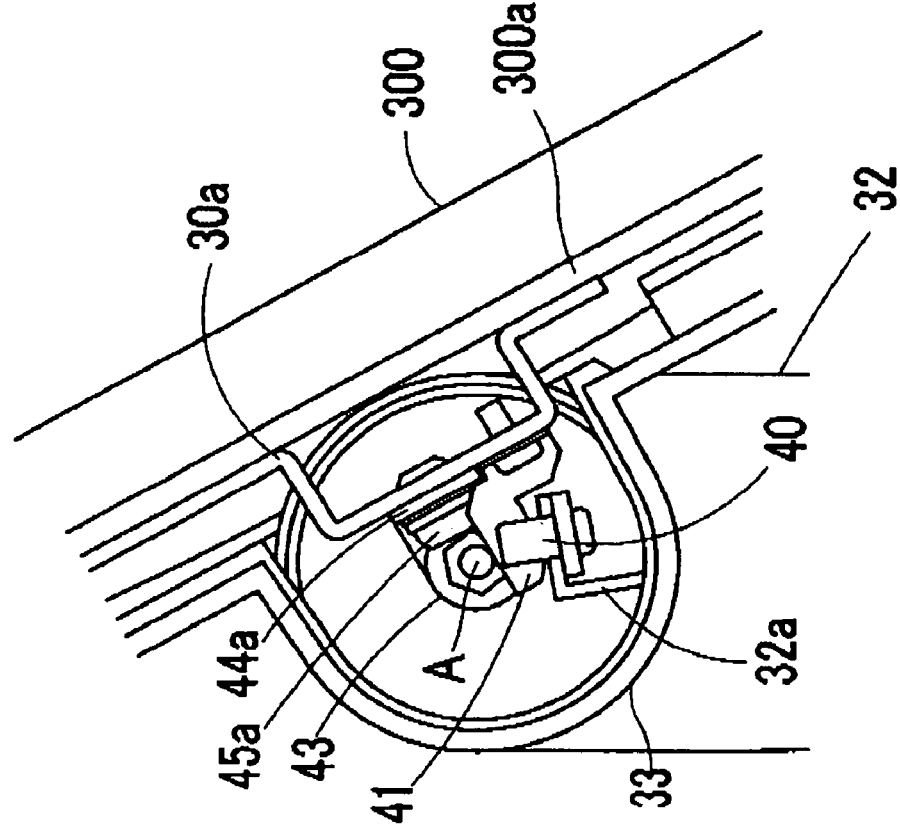

FIG.9

PRICE LIST

| | NON-COATING | ANTIREFLECTIVE COAT | WATER-REPELLENT COAT | ULTRA-WATER-REPELLENT COAT | ANTIFOULING COAT |
|---|---|---|---|---|---|
| NONCOMPRESSED LENS | **** | **** | **** | **** | **** |
| COMPRESSED LENS | **** | **** | **** | **** | **** |
| ASPHERIC LENS | | **** | **** | **** | **** |
| DOUBLE-ASPHERIC LENS | | **** | **** | **** | **** |

COLOR: * * * *
UV COAT: * * * * *

PROFITABLE INFORMATION !!!
OFFER NOW * * * * * AS FREE BONUS !

OPTOMETER

BACKGROUND OF THE INVENTION

1. Field of the Invention

The present invention relates to an optometer (a vision tester) for subjective examination (measurement) of refractive power and others of an examinee's eye.

2. Description of Related Art

There is an optometer (a vision tester) having a main unit (a phoropter) arranged to dispose optical elements such as a sphere lens and a cylinder lens in front of an examinee's eye and a controller, and the optometer being structured to perform subjective examination (far vision test) on refractive power and others of the examinee's eye by allowing an examinee to view an optotype presented at a predetermined distance for far vision test apart from the examinee's eye. This optometer is adapted to change the optical elements to be disposed in front of the examinee's eye by operation of the controller by an examiner. The controller is provided with a display which displays various kinds of optometry information such as information on the optical element disposed in front of the examinee's eye.

Recently, an optometer capable of performing near vision test using this type of controller (an optometer in which the display of the controller is also used as an optotype presenting unit for near vision test) has been proposed (see Japanese unexamined patent publication No. 9(1997)-299332). However, this apparatus is structured so that the entire controller or the display separately located from a switch panel (an operating part) of the controller is turned to the examinee. It is therefore poor in usability.

BRIEF SUMMARY OF THE INVENTION

The present invention has been made in view of the above circumstances and has an object to provide an optometer with an easy-to-use controller.

Additional objects and advantages of the invention will be set forth in part in the description which follows and in part will be obvious from the description, or may be learned by practice of the invention. The objects and advantages of the invention may be realized and attained by means of the instrumentalities and combinations particularly pointed out in the appended claims.

To achieve the above purpose, the invention provides an optometer for subjectively examining refractive power of an examinee's eye, comprising: a phoropter which selectively disposes an optical element in front of the examinee's eye; a controller having a switch panel for transmitting a signal to the phoropter and a horizontally extending rotation axis; a display rotatable about the rotation axis of the controller, orientation of the display being changeable by its rotation between a side with the switch panel and a side without the switch panel; and a control part which controls a display screen of the display to appear in a constant orientation irrespective of whether the display is reversed upside down by its rotation.

BRIEF DESCRIPTION OF THE DRAWINGS

The accompanying drawings, which are incorporated in and constitute a part of this specification illustrate an embodiment of the invention and, together with the description, serve to explain the objects, advantages and principles of the invention.

In the drawings,

FIGS. 3A and 3B are schematic external views of a controller of the optometer;

FIGS. 5A and 5B are schematic structural views of the rotation mechanism of the display unit;

FIG. 9 is a view showing an example of a screen presenting a price list of spectacle lenses.

DETAILED DESCRIPTION OF THE PREFERRED EMBODIMENTS

A detailed description of a preferred embodiment of the present invention will now be given referring to the accompanying drawings.

Figure 1:
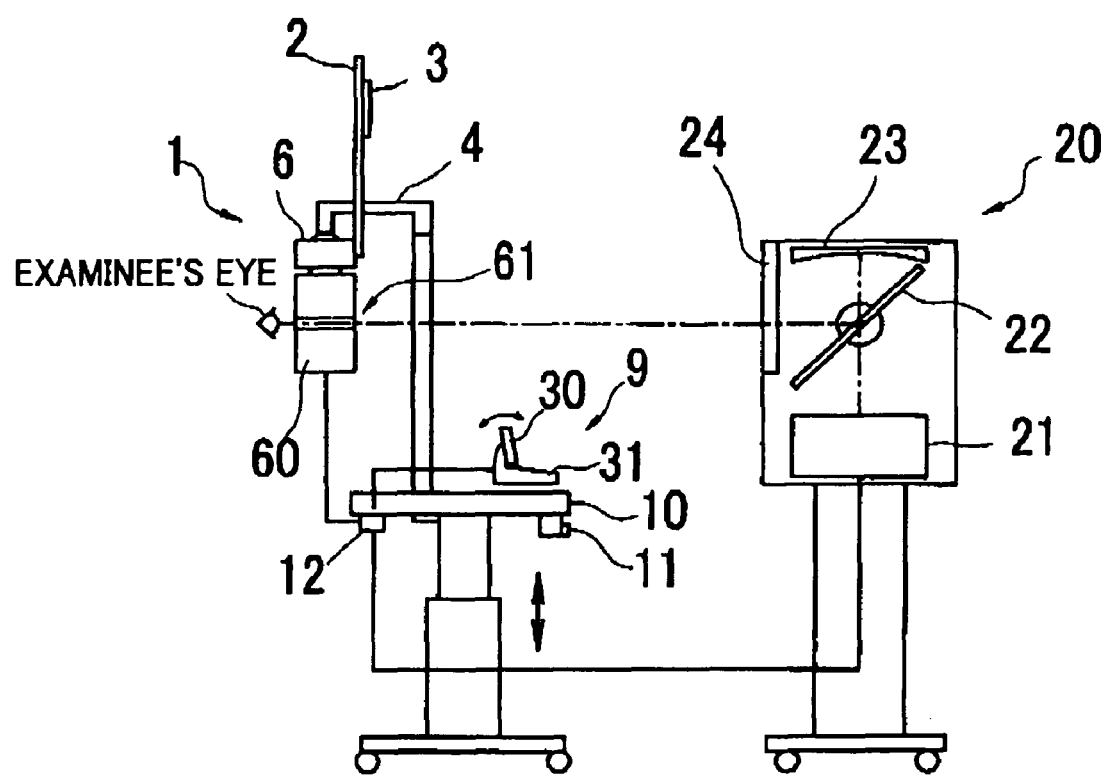
FIG. 1 is a schematic structural view of an optometry system including an optometer in a preferred embodiment of the present invention.
Figure 2:
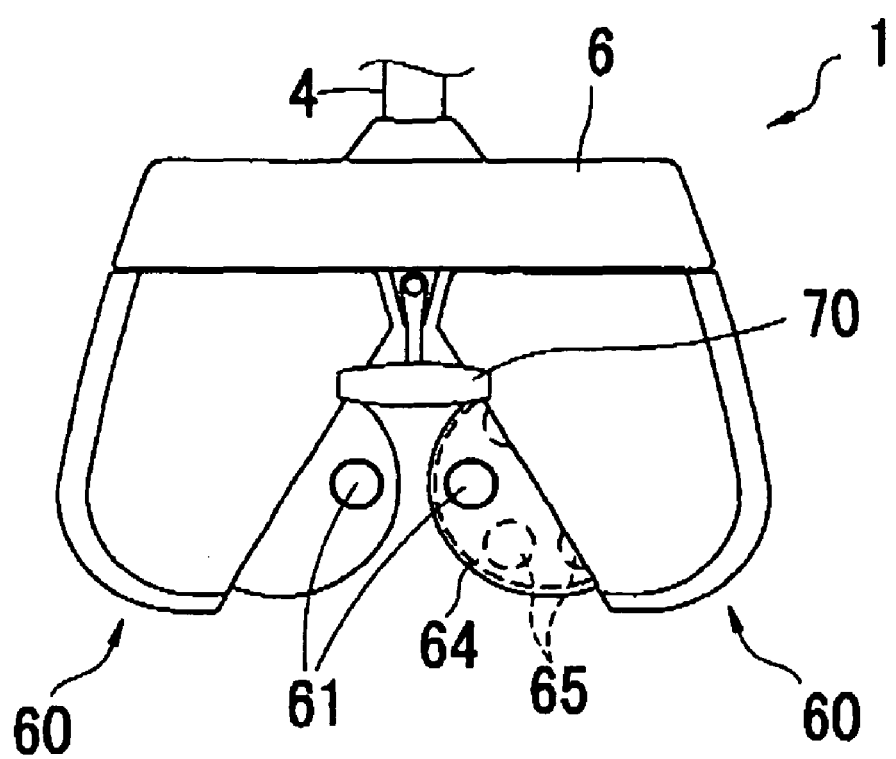
FIG. 2 is a schematic external view of a main unit (a phoropter) of the optometer, viewed from an examinee side.

FIG. 1 is a schematic structural view of an optometry system including an optometer (a vision tester) in the preferred embodiment of the present invention. FIG. 2 is a schematic external view of a main unit (a phoropter) 1 of the optometer, viewed from an examinee side. FIGS. 3A and 3B are schematic external views of a controller 9 of the optometer.

The phoropter 1 of the optometer includes a pair of lens chamber units (optometric units) 60 symmetrical in right and left configuration each having a test window 61, and a supporting part 6 which supports the lens chamber units 60 in a hanging state. The supporting part 6 is internally provided with a movement mechanism 50 (see FIG. 10) including a sliding mechanism for adjusting a distance between the lens chamber units 60 and a convergence mechanism for adjusting a convergence angle of the lens chamber units 60. A forehead rest 70 attached to the supporting part 6 is used for supporting the head of an examinee to fix the examinee's eye(s) in a predetermined test position.

Each of the lens chamber units 60 holds, in its casing, a plurality of rotatable lens disks 64 in each of which a plurality of various optical elements 65 (including an opening) such as a sphere lens, a cylinder lens, a cross-cylinder lens, a red filter, a green filter, a polarizing filter, and a shielding plate are circumferentially arranged (held) on the same circle. These disks 64 are rotated individually by a rotation mechanism 63 (see FIG. 10) to dispose one of the optical elements 65 of each disk 64 in the test window 61.

The phoropter 1 is supported above a table 10 by a support arm 4 attached to the table 10. By operation of an up-down switch 11, the height of a top plate of the table 10, that is, the height of the phoropter 1 is adjusted by a movement mechanism not shown.

An optotype presenting device 20 for far vision test (FIG. 1 shows a schematic internal structure thereof) is placed forward at a predetermined far-vision-test distance apart from the phoropter 1. This optotype presenting device 20 is internally provided with an optotype presenting part 21 which presents various optotypes, a half mirror 22, a concave mirror 23, a window 24, and others. Optotype light from the optotype presenting part 21 partly passes through the half mirror 22 and is reflected by the concave mirror 23, and further partly reflected by the half mirror 22 toward the examinee's eye through the window 24.

A rod 2 on which an optotype presenting unit 3 for near vision test is mounted is attached to the supporting part 6. The optotype presenting unit 3 has a chart on which a plurality of optotypes is drawn. This unit 3 is movable on the rod 2 along its length direction. The rod 2 is held in an up position (shown in FIG. 1) except during the near vision test. During the near vision test, the rod 2 is moved down to a horizontal position and the optotype presenting unit 3 is moved to a forward position at a predetermined distance for near vision test apart from the lens chamber units 60.

A relay unit 12 is connected to the phoropter 1, the optotype presenting device 20, and a controller 9 which will be mentioned later. Based on signals from a control part 130 of the controller 9, a control part 120 of the relay unit 12 transmits signals to a control part 140 of the phoropter 1 and a control part 150 of the optotype presenting device 20.

In the present embodiment, the controller 9 serving as an operating unit for the phoropter 1 is also used as an operating unit for the optotype presenting device 20. A supporting part 32 extending upward from a base unit 31 of the controller 9 rotatably supports a display unit 30 provided with a color liquid crystal display (monitor) 300. The display 300 is of a touch panel function enabling switch operations even on a display screen (which will be mentioned later in more detail). A switch panel (operating part) 35 provided on the base unit 31 includes various kinds of switches (which will be mentioned later in more detail).

Figure 4:
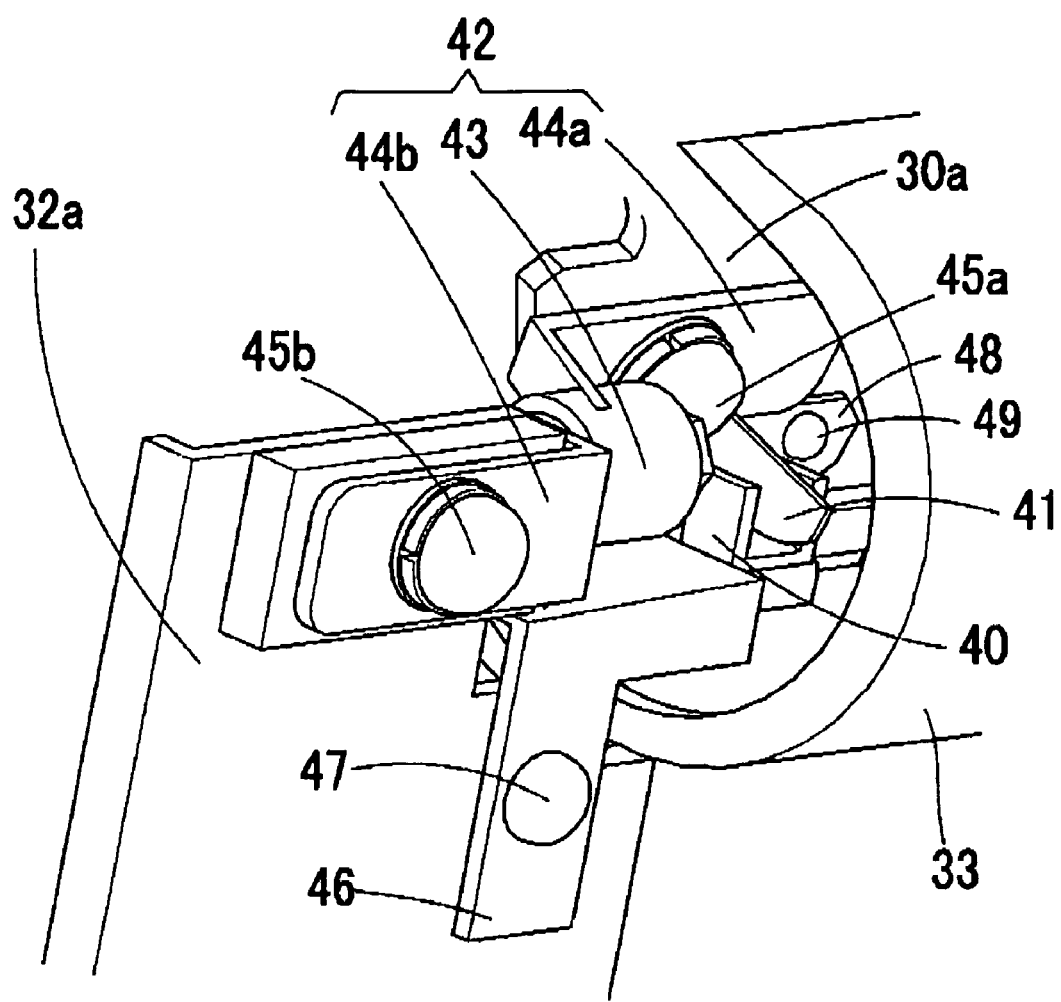
FIG. 4 is a schematic structural view of a rotation mechanism of a display unit.

A rotation mechanism of the display unit 30 will be explained. FIG. 4 and FIGS. 5A and 6B are schematic structural views of the rotation mechanism of the display unit 30. A cylindrical engagement portion 33 formed in the rear of the display unit 30 is engaged between two cylindrical engagement portions 34 provided at upper right and left ends of the supporting part 32. Inside these engagement portions 33 and 34, a rotary hinge 42 is arranged 80 that one hinge plate 44a rotatable with respect to a joint 43 of the hinge 42 is secured by a screw 45a to a plate 30a fixed to a base plate 300a of the display 300 and the other hinge plate 44b rotatable with respect to the joint 43 is secured by a screw 45b to a base plate 32a inside the supporting part 32. With this configuration, the display unit 30 can be rotated about a horizontally extending axis A which is a rotational central axis of the hinge 42. This structure makes it possible to change the orientation of the display unit 30 between a position where the display 300 faces to the side with the switch panel 35 (an examiner side) (i.e. the position in FIGS. 3A, 4, and 5A) and a position where the display 300 faces to the side without the switch panel 35 (an examinee side) (i.e. the position in FIGS. 3B and 5B).

A mechanism for detecting the orientation of the display unit 30 (the display 300) will be explained. A U-shaped photosensor (photointerrupter) 40 is attached to a plate 46 secured to the base plate 32a by a screw 47 and a shielding plate 41 is attached to a plate 48 secured to the plate 30a by a screw 49. While the display 300 is oriented to face to the examiner side (FIG. 5A), the shielding plate 41 is inserted in the photosensor 40. While the display 300 is oriented to face to the examinee side (FIG. 5B), the shielding plate 41 is moved out of the photosensor 40. Accordingly, the orientation of the display unit 30 (the display 300) is detected based on a detection signal of the photosensor 40.

Figure 6:
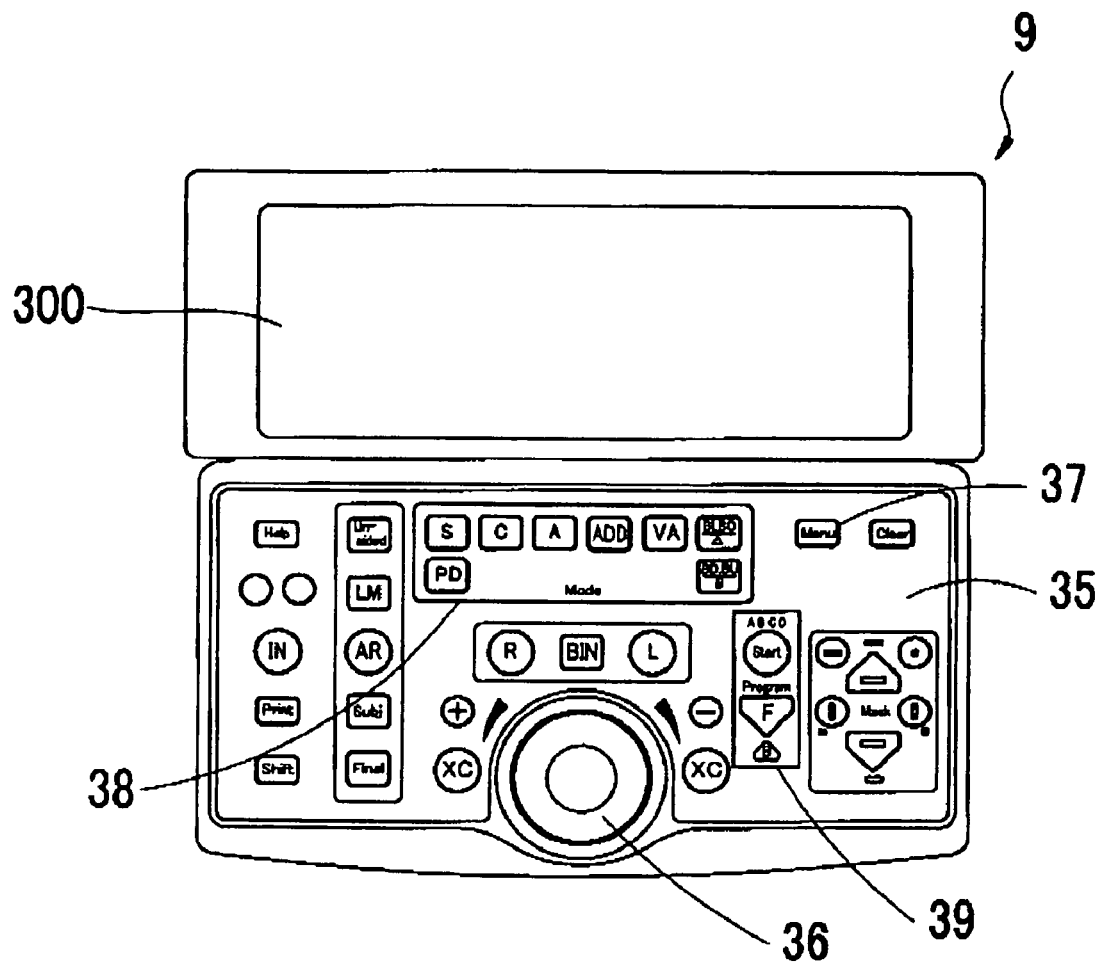
FIG. 6 is a schematic external view of the controller viewed from above.

The switch panel 35 will be explained. FIG. 6 is a schematic external view of the controller 9, viewed from above. The switch panol 35 is provided with a dial switch 36 for increasing/decreasing numeric values, a [Menu] switch 37 for setting and changing a display mode, a [Mode] switch 38 for switching to a mode of changing data on for example sphere power [S], cylinder power [C], and a cylinder axis angle [A], a [Program] switch 39 including a [Start] switch for an optometry program, and other switches. A [PD] switch of the [Mode] switch 38 is used to adjust the positions of the right and left test windows 61 to an interpupillary distance of the examinee. When the [PD] switch is operated (pressed) and successively the dial switch 36 is operated (turned), the distance between the lens chamber units 60 is adjusted by the movement mechanism 50. An [ADD] switch of the [Mode] switch 38 is used to adjust the positions of the right and left test windows 61 to the convergence angle of the examinee. When the [ADD] switch is operated (pressed), the convergence angle between the lens chamber units 60 is adjusted by the movement mechanism 50.

Figure 7:
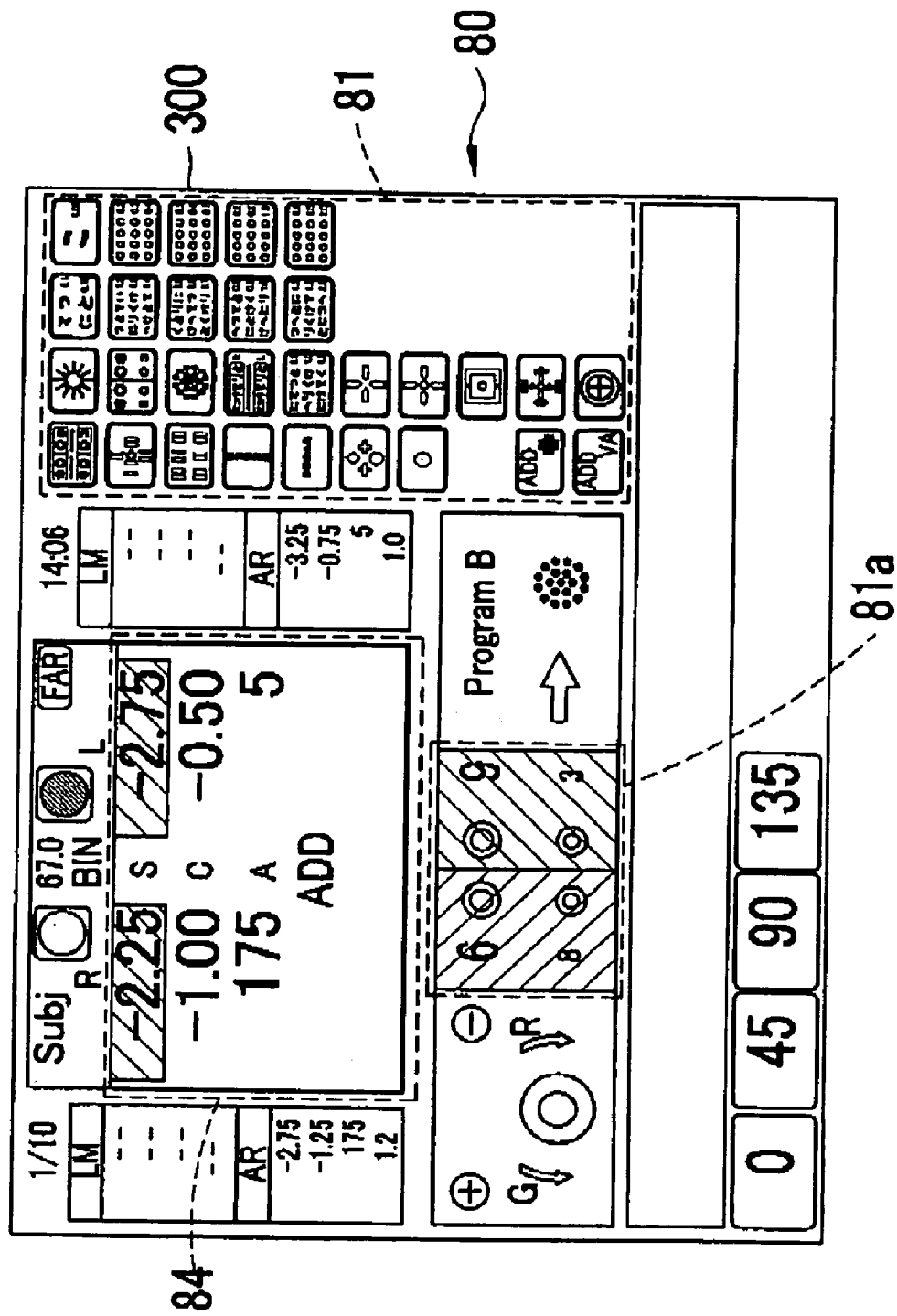
FIG. 7 is a view showing an example of a screen for examiner, displayed on the display.

A display screen on the display 300 will be explained. FIG. 7 is a view showing an example of a screen for examiner, displayed on the display 300. A screen 80 for examiner displayed on the display 300 includes information on the optical elements 65 disposed in the right and left test windows 61, information on refractive power measured by an external device and input to the present device (an [LM] frame indicates information on refractive power of examinee's own spectacles or contact lenses measured by a lensmeter, and an [AR] frame indicates information on refractive power of the examinee's eye measured by an objective refractive power measurement device called auto-refractometer), and other information. Icons (touch-panel switches) 81 are operated (touched) to select (switch) optotypes to be presented by the optotype presenting device 20. Information on the currently presented (selected) optotypes is displayed on a frame 81a. The touch panel function of the display 300 is used for operation of the optotype presenting device 20. Accordingly, even when the optotype presenting device 20 is replaced with a device of a different type, this device can easily be operated if only displaying software for the display 300 is changed to a corresponding one. Displayed in a frame 84 is information on the optical elements 65 disposed in the right and left test windows 61.

Figure 8:
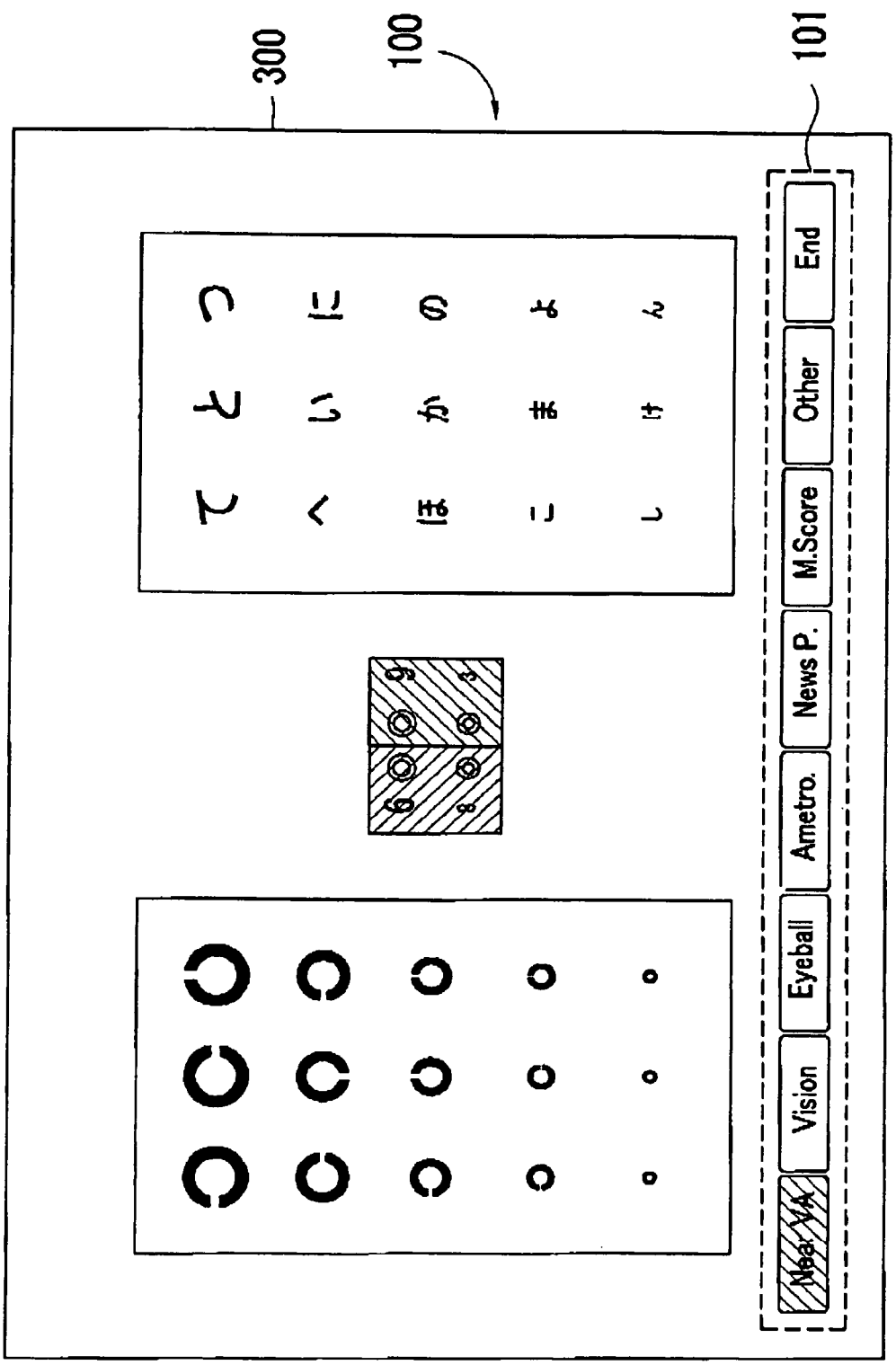
FIG. 8 is a view showing an example of a screen for examinee, displayed on the display.

FIG. 8 is a view showing an example of a screen for examinee, displayed on the display 300. Icons 101 are operated (touched) to select (switch) a screen 100 for examinee to be displayed on the display 300. The screen 100 in FIG. 8 is an optotype presenting screen (selected by a [Near VA] icon) for near vision test. Other screens 100 may include a screen (selected by a [Vision] icon) showing an examinee as to differences in vision between myopia, hyperopia, astigma, and others, a screen (selected by an [Eyeball] icon) showing a structural drawing of an eye, a screen (selected by an [Ametro.] icon) showing a drawing of refractive power of an eye with myopia, hyperopia, astigma, and others, a newspaper screen (selected by a [News P.] icon) and a musical score screen (selected by an [M. Score] icon) which are used for documents to be viewed by an examinee at a near vision distance (a short distance), and other screens. Using these screens 100, the examiner can explain about refractive errors and perform simple checks as to differences in vision, etc. With the touch of an [Other] icon, further, a screen showing sales promotional materials such as a price list of spectacle lenses (see FIG. 9). The screen 100 may be arbitrarily configured.

Figure 10:
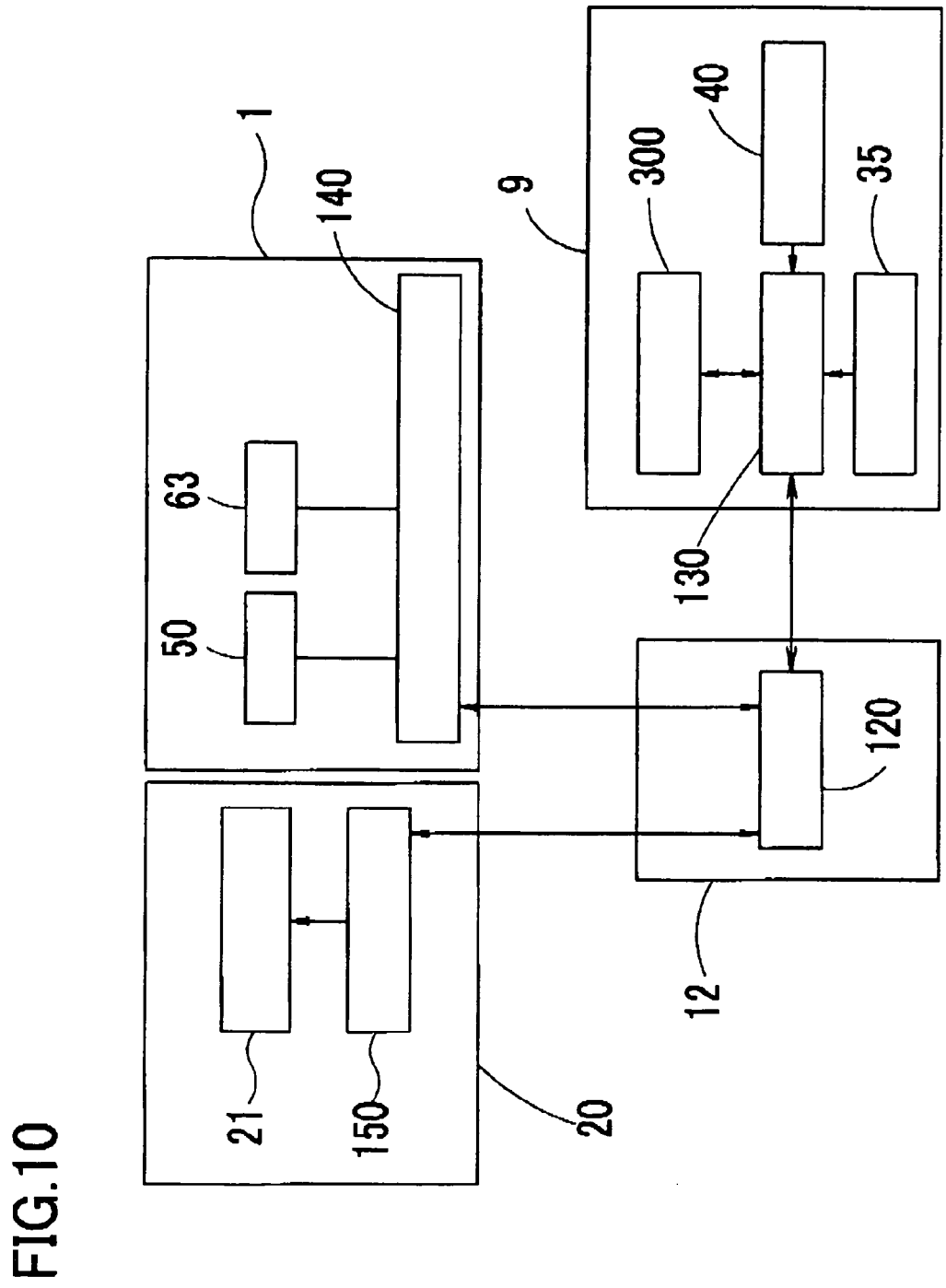
FIG. 10 is a schematic block diagram of a control system of the optometry system.

The operation of the optometry system having the above structure will be explained below. FIG. 10 is a schematic block diagram of a control system of the optometry system. Preferably, prior to the test, refractive power (sphere power, cylinder power, and a cylinder axis angle) and an interpupillary distance of the examinee's eyes are measured by an objective refractive power measurement device not shown. By operation of an [AR] switch on the controller 9, those measured values are input into the control part 130 of the controller 9, the control part 140 of the phoropter 1 and the control part 150 of the optotype presenting device 20 via the control part 120 of the relay unit 12, respectively. In the case where the examinee wears spectacles or contact lenses, its refractive power (sphere power, cylinder power, and a cylinder axis angle) is measured by a lensmeter not shown. By operation of an [LM] switch on the controller 9, those measured values are input into the control part 130 and the control parts 140 and 150 via the control part 120. The control part 140 controls the movement mechanism 50 based on the input interpupillary distance to adjust the distance between the lens chamber units 60. To additionally adjust the lens chamber units 60, the [PD] switch on the controller 9 and the dial switch 36 have to be operated, so that the control part 140 further controls the movement mechanism 50 to adjust the distance between the lens chamber units 60.

In the test, the control part 140 controls the rotation mechanism 64 based on the input refractive power to dispose one of the plurality of optical elements 65 arranged in each disk 64, into each test window 61. The control part 150 controls the optotype presenting unit 21 based on the input refractive power to present an appropriate optotype.

When the optotype presented by the optotype presenting device 2 is to be changed, the icons 81 on the screen 80 for examiner are operated and thus the control part 130 transmits a command signal to the control part 150 via the control part 120. The control part 150 controls the optotype presenting unit 21 based on the command signal to present a selected optotype. At this time, the control part 130 displays the information on the selected optotype in the frame 81a.

When the optical element 65 disposed in each test window 61 is to be changed, an [S] switch, a [C] switch, an [A] switch, and others of the [Mode] switch 38 on the controller 9 and the dial switch 36 are operated. Thus, the control part 130 transmits a command signal to the control part 140 via the control part 120. The control part 140 controls the rotation mechanism 63 based on the command signal to dispose a selected one of the optical elements 65 in the test window 61. At this time, the control part 130 displays the information on the selected optical element 65 in the frame 84.

When the refractive power of the examinee's eye are obtained by presenting optotypes, disposing the optical elements 65, and so on, the [Menu] switch 37 is operated to display a menu screen not shown on the display 300. By operation of the icon appearing on this menu screen, the screen 100 for examinee is called up. When the screen 100 is displayed, the display unit 30 is rotated to turn the display 300 from a position facing to the switch panel 35 side (the examiner side) to a position facing to the opposite side (the examinee side). When the display unit 30 is rotated, the display screen of the display 300 is displayed in a vertically and horizontally inverted state, or turned 180°, from the display screen at the position facing to the examiner side. This inversion is performed by the control part 130 which detects the orientation of the display 300 based on a detection signal of the photosensor 40 and controls the display screen of the display 300. Accordingly, even when the display 300 is turned upside down by rotation of the display unit 30, the orientation of the display screen of the display 300 can be constant.

When the display 300 is turned toward the examinee, the examiner moves to the examinee side and operates the icons 101 to display various screens 100. To return the screen 100 for examinee to the screen 80 for examiner, the [Menu] switch 37 and others are operated again.

While the screen 100 is displayed on the display 300, the control part 130 does not accept signals from the [Mode] switch 38, [Program] switch 39, and others. This makes it possible to prevent improper operations of the system (device).

In the present embodiment, the display screen on the display 300 is changed from the screen for examiner to the screen for examinee when the [Menu] switch 37 and others are operated. Alternatively, the display screen may be changed from the screen for examiner to the screen for examinee by rotation of the display unit 30 to turn the display 300 from the position facing to the examiner side to the position facing to the examinee side. In this case, the display screen is changed from the screen for examinee to the screen for examiner when the display 300 is returned to an original position (orientation).

In the present embodiment, further, acceptance of signals from the switch panel 35 is restricted as soon as the display screen on the display 300 is changed from the screen for examiner to the screen for examinee. Alternatively, the switch operation may be restricted when the display 300 is turned to the position facing to the examinee side.

The display unit 30 of the controller 9 may be provided with a small display in the rear of the display 300. On this small display, as with the display 300, the screen for examines is displayed when the display screen on the display 300 is changed from the screen for examiner to the screen for examinee. Accordingly, the examiner is not required to move to the examinee side even while the display 300 faces to the examinee side.

While the presently preferred embodiment of the present invention has been shown and described, it is to be understood that this disclosure is for the purpose of illustration and that various changes and modifications may be made without departing from the scope of the invention as set forth in the appended claims.

What is claimed is:

1. An optometer for subjectively examining refractive power of an examinee's eye, comprising:
    a main unit, including a pair of lens chamber units, which selectively disposes an optical element in front of the examinee's eye;
    a controller having a base unit, a supporting part extending upward from the base unit, a switch panel provided on the base unit for transmitting a signal to the main unit, and a control part;
    a display unit on a front surface of which a display screen is provided, the display unit being supported by the supporting part in such a manner as to be rotatable about a horizontally extending axis by a hinge mechanism located in approximately a center of a rear side of the display unit, so that orientation of the display screen is changeable between a first side with the switch panel and a second side without the switch panel by the rotation of the display unit and a top and a bottom of the display screen facing to the first side and a top and a bottom of the display screen facing to the second side are reversed; and
    a sensor unit for detecting at least one of whether the orientation of the display screen is in the first side and whether the orientation of the display screen is in the second side;
    wherein the control part controls a display of the display screen based on a detection result of the sensor unit to allow a display image on the display screen oriented to face to the second side to appear in the same direction as a display image on the display screen oriented to face to the first side even when the top and the bottom of the display screen facing to the first side and the top and the bottom of the display screen facing to the second side are reversed.

2. The optometer according to claim 1, wherein the control part changes the display image on the display screen based on the detection result of the sensor unit to an image for an examiner including information of the disposed optical element when the orientation of the display screen is in the first side and to an image for the examinee including at least one of an optotype and a document to be presented to the examinee's eye when the orientation of the display screen is in the second side.

3. The optometer according to claim 2, wherein the image for the examinee includes at least one of an optotype presenting image for a near vision test and a document image to be viewed by the examinee's eye at a near vision distance.

4. The optometer according to claim 2, wherein the display screen has a touch panel function, and
the image for the examiner includes a switch for selecting an optotype for a far vision test, to be presented to the examinee's eye.

5. The optometer according to claim 2, wherein the control part does not accept part of signals from the switch panel when the display image on the display screen is changed to the image for the examinee.

6. The optometer according to claim 1, wherein the control part does not accept part of signals from the switch panel when the orientation of the display screen is changed to the second side.

7. The optometer according to claim 1, wherein the display unit includes a small display screen on a side opposite from the display screen, the small display screen being arranged to display a same image as the display image on the display screen.

8. The optometer according to claim 1, wherein the sensor unit detects the position of the display unit with respect to the supporting part to detect at least one of whether the orientation of the display screen is in the first side and whether the orientation of the display screen is in the second side.

9. The optometer according to claim 1, wherein the sensor unit includes a photosensor which detects the rotation of the hinge mechanism.

10. The optometer according to claim 1, wherein the sensor unit is a photointerrupter including a photosensor and a shielding plate.

* * * * *